United States Patent
Lawes et al.

[11] Patent Number: 5,171,286
[45] Date of Patent: Dec. 15, 1992

[54] CEMENTED TAPER LOCK ACETABULAR CUP

[75] Inventors: Peter Lawes, Maidenhead; Robin S. M. Ling, Exeter, both of England

[73] Assignee: Howmedica International Inc., Shannon, Ireland

[21] Appl. No.: 736,150

[22] Filed: Jul. 26, 1991

[30] Foreign Application Priority Data

Aug. 8, 1990 [GB] United Kingdom ............... 9017403

[51] Int. Cl.⁵ .............................................. A61F 2/32
[52] U.S. Cl. .................................................... 623/22
[58] Field of Search ........................ 623/22, 23, 18, 16

[56] References Cited

U.S. PATENT DOCUMENTS 4,642,124  2/1987  Cooke ................................ 623/23

FOREIGN PATENT DOCUMENTS

| | | | |
|---|---|---|---|
| 0120595 | 10/1984 | European Pat. Off. | 623/23 |
| 0225819 | 6/1987 | European Pat. Off. | 623/23 |
| 0289192 | 11/1988 | European Pat. Off. | 623/22 |
| 2247721 | 4/1974 | Fed. Rep. of Germany | 623/22 |
| 3630276 | 3/1988 | Fed. Rep. of Germany | 623/23 |
| 2622432 | 5/1989 | France | 623/22 |
| 0426096 | 6/1967 | Switzerland | 623/22 |
| 2104391 | 3/1983 | United Kingdom | 623/22 |

Primary Examiner—David Isabella
Attorney, Agent, or Firm—Peter C. Richardson; Lawrence C. Akers; Raymond W. Augustin

[57] ABSTRACT

An acetabular cup for use in a total hip prosthesis includes an implant/cement interface portion for location in a cement mantle. The cup has an enclosure element for allowing the cup to slide lengthwise to re-engage itself in the cement mantle to accommodate creep or movement thereof. Thus, should there be a tendency for the cup to become loose, the construction according to the invention is intended to relock the cup within the cement mantle. Thus, if the bone remodels, then the cement mantle will creep to re-adapt itself to the bone and the implant will re-engage in the cement mantle accommodating to the movement of the cement. If the bone cement is too highly stressed in places, it will creep in order to relieve this stress and the implant will re-settle.

10 Claims, 2 Drawing Sheets

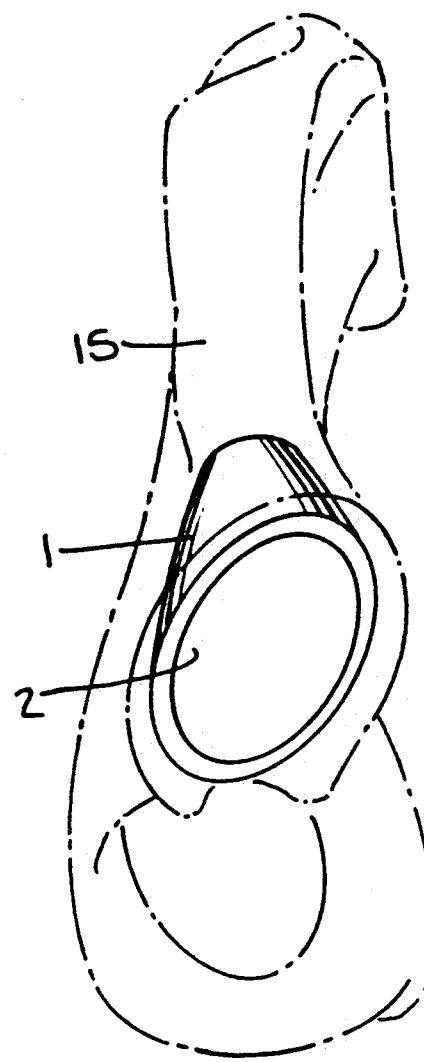
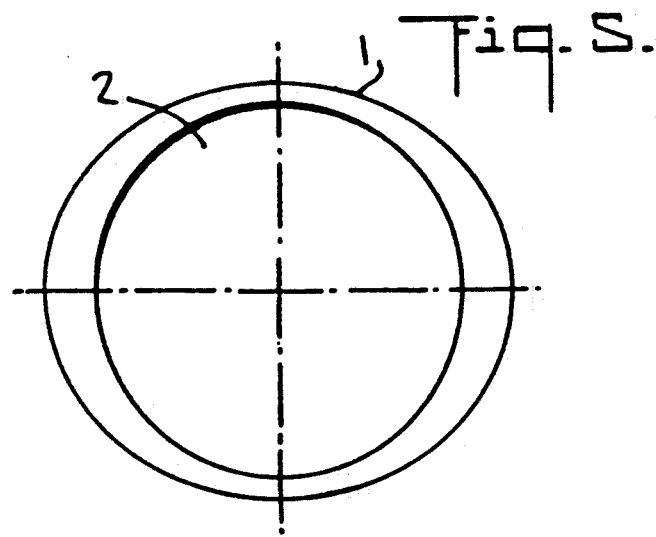

1

CEMENTED TAPER LOCK ACETABULAR CUP

BACKGROUND OF THE INVENTION

This invention relates to a cemented acetabular cup capable of re-locking itself in the acetabulum should movement occur between the acetabulum and the cemented prosthesis.

Loosening of acetabular cups is a major problem in total hip surgery and the object of the present invention is to produce an acetabular cup which is less likely to loosen.

SUMMARY OF THE INVENTION

According to the present invention, an acetabular cup is provided for use in a total hip prosthesis. The cup includes an outer portion for location in a patient's pelvis and is held in place in a cement mantle. The cup includes an enclosure element for allowing the outer portion of the cup to move further into the pelvis and re-engage itself to accommodate creep or movement thereof.

Thus, should there be a tendency for the cup to become loose, a construction according to the present invention is intended to relock the cup within the cement mantle. Thus, if the bone remodels, the cement mantle will creep to readapt itself to the bone and the implant will re-engage in the cement mantle accommodating to the movement of the cement. If the bone cement is too highly stressed in places, it will creep in order to relieve this stress and the implant will resettle.

Preferably, the outer portion consists of a tapered element having a smooth surface in longitudinal directions so that when the implant resettles it will tend to lock due to the taper. The tapered element is preferably substantially conically shaped with an apex at its proximal end and includes anti-rotation elements.

Thus, the anti-rotation means can be provided on the element by multi-facets, flats, keyways or ridges or the element can have an oval or asymmetric cross-section. It is important that the various anti-rotation elements only extend in a direction or directions to prevent rotation and not in any spiral or circumferential direction that would tend to resist subsidence and re-locking of the implant within the cement mantle. Any movement, when it must occur, must not be between the cement and the bone and it is important therefore to protect the cement bone interface from disturbance.

In a preferred construction, an enclosure is provided for housing the proximal end of the tapered element. The enclosure has a control element for allowing the proximal end to move further into a void within the enclosure subsequently to fitting.

This enclosure, which acts as a void-creator, is added to the end of the element as it is not desirable to bring the end of the element down to a sharp point. However, it is also not desirable to form the end as a blunt point because it can engage cement and resist the taper lock re-engagement. The enclosure can be in the form of a cup, one end (proximal end) of which is closed and in which the control element is in the form of a collar at a mid point or at the other end (distal end) of the cup.

In another embodiment, the walls of the cup enclosure extend outwardly over the whole outer surface area of the acetabular cup. The enclosure can be made from material similar to bone cement material, for example, an acrylic material such as polymethylmethacrylate, to make it fully compatible with the bone cement and in effect provides a preformed cement mantle.

The outer surface of the outer portion is made as smooth as possible, for example, by polishing a metal implant in order to reduce the friction and purchase between the implant and the cement. There must be no ridges, grooves, undercuts, matt finishes, or rough surfaces that would give a grip on the cement or the enclosure. Ideally the only load transfer from the element to the cement or the enclosure is through a comprehensive force normal to the interface surface between them.

The cup can have a bearing insert if desired. Thus, for example, the element can be in the form of a metal backing with a polyethylene bearing insert within it. Alternatively, the insert and fixation surface could be one and the same material. For example, a coating could be put on the bearing surface to articulate with a femoral stem or a coating could be put on the implant/cement interface portion merely to prevent adhesion and minimize friction with the cement. The invention also includes a total hip prosthesis incorporating an acetabular cup as set forth above.

BRIEF DESCRIPTION OF THE DRAWINGS

The invention can be performed in various ways and some embodiments will now be described by way of example and with reference to the accompanying drawings in which:

FIG. 3 is a diagrammatic view showing how the cup according to the invention can be implanted in the pelvis of a patient;

FIG. 5 is a plan view of an acetabular cup which is slightly oval in cross-section to prevent rotation.

DESCRIPTION OF THE PREFERRED EMBODIMENT

Figure 1:
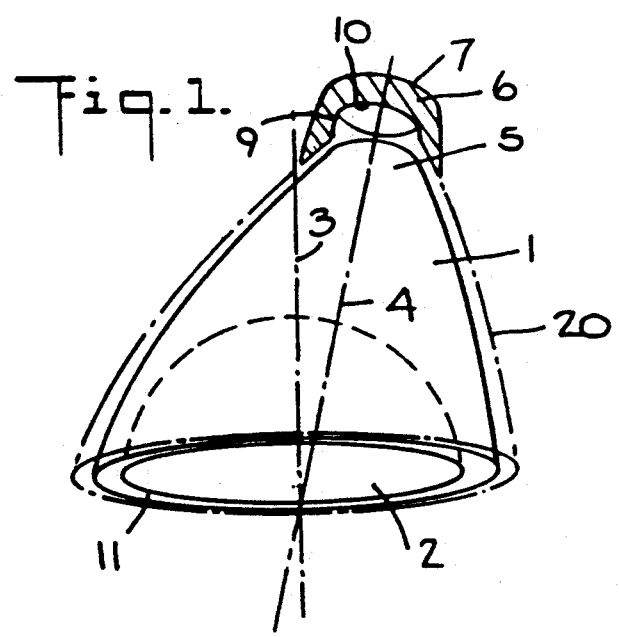
FIG. 1 is a diagrammatic view of an acetabular cup according to the invention.
Figure 2:
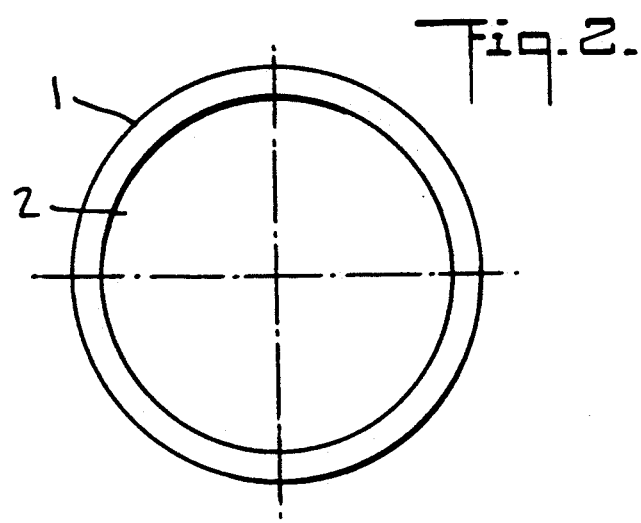
FIG. 2 is an end view of the cup shown in FIG. 1.

As shown in FIG. 1, an acetabular cup 1 for use in a total hip prosthesis has an outer surface portion indicated by reference numeral 1'. This outer portion 1' consists of a tapered element having a smooth surface in longitudinal directions and, in the preferred embodiment, is substantially conical. It will be seen that the outer surface of outer portion 1 is not co-axial with a bearing surface 2 provided within the cup. The axis of the bearing surface is indicated by reference numeral 3 and the general axis of conical outer portion 1, by reference numeral 4. The proximal end 5 of the element is housed within an enclosure element 6 in the form of an acrylic void creator.

Enclosure element 6 is provided as a cup having a closed end 7, an open end 8 and control element formed by a collar 9. The open end of collar 9 is provided with a taper. This device is located by pushing it over the proximal end 5 of the conical outer portion 1, so that there is a gap between the distal end and the inner surface 10 of the closed end of the cup, thus creating a void between them. The void creator in the form of enclosure element 6 is added to the top of the acetabular cup as it is not desirable to bring the proximal end of the conical outer portion 1' to a sharp point, but neither is it desirable that a blunt point can engage cement and resist the taper lock re-engagement to be described hereafter.

In an alternative construction, the enclosure element 6 is formed to extend a length to envelop the whole of the outer surface of outer portion 1' as shown in broken lines 20 in FIG. 1. In this arrangement the control means can be provided by any convenient part of the engaging surface. The total enclosure of the outer surface of cup-shaped outer portion 1' allows cup 1 to move inwardly of enclosure element 6 under load. The void creator in the form of enclosure element 6 is therefore in the form of a preformed sheath and is made from a material similar to bone cement material, for example, polymethylmethacrylate. It is, in effect, another layer of cement, but it is not secured to the cup.

The thickness of this preformed sheath can be as small as possible, provided it is strong enough not to crack during implantation and, for example, it can be between 0.5 mm and 5 mm and is preferably about 1 mm for practical use. It will be appreciated that the sheath is molded separately and is shaped to fit a particular size of cup 1.

By preforming such a sheath there is a reduced adhesion between what is in effect the bone cement, provided by the sheath itself, and the outer surface of the implant, thus not only providing better sliding of the implant within the cement mantle but relieving any loads which are likely to occur between the cement mantle and the bone.

It will be appreciated that the bearing surface 2 can house an inner bearing element or can be coated or made in any manner desired. In the arrangement shown, and as referred to above, the angle of the outer end surface 11 of the acetabular cup is angled in relation to the axis 3 of the bearing surface 2.

FIG. 3 shows how such an acetabular cup can be implanted in a patient's pelvis so that the conical outer portion 1' points along what is known as the sacral bar 15. On the pelvis there is a substantial bony bar passing from the acetabulum along the posterior medial portion of the ilium up to the joint with the sacrum. In order to prepare the acetabulum to accept the acetabular cup according to the invention, part of the bone in the direction of this bony bar 15 is reamed out to prepare a suitable tapering cavity. Acrylic enclosure element 6 and the mating tip of the conical element are placed co-axially inside this pre-prepared cavity pointing along the center of the bony bar.

The acetabular cup is held in the pre-prepared cavity by bone cement which adheres to the bone and to the outer surface of the cup. Due to the smooth surface of the cup, however, the adhesion between it and the cement is not strong and thus if there is any creep in the cement, caused for example by movement of the bone, the cup will tend to sink further into the cement and re-establish itself due to the taper of its outer surface. The acrylic enclosure element 6 (not shown in FIG. 3) enables the cup to sink deeper into the cement with its proximal end being accommodated in the void 10, thus preventing splitting of the cement or resistance to inward movement.

It will be appreciated that there must be no ridges, grooves, undercuts, matt finishes, or rough surfaces that will give a grip on the cement, and the outer surface of outer portion 1' is therefore deliberately finished to minimize friction and perches between it and the cement. If the implant is metal, then the outer surface can be polished.

With other known kinds of implants, when loosening starts in the cement the loosening gradually gets worse and the attractive feature of the present invention is that movement tends to be self-limiting, that is it is non-progressive.

Figure 4:
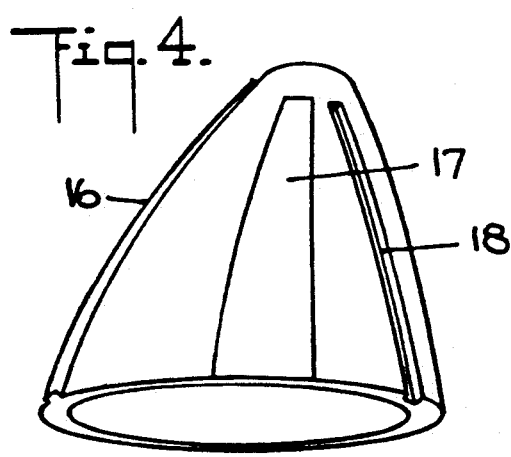
FIG. 4 shows a cup carrying various anti-rotation features.

As the outside of the cup-shaped outer portion 1 is not co-axial with the bearing surface, there may be a tendency to turn, and anti-rotation means can be provided as shown in FIGS. 4 and 5. Thus, in FIG. 4 an acetabular cup 1 is shown which is provided with three different types of anti-rotation features. These three features may be used individually or in combination on a particular cup. Reference numeral 16 indicates a ridge, one or more of which can be provided on the outer surface, reference numeral 17 indicates a flat or facet, again one or more of which can be provided, and reference numeral 18 indicates a groove, again one or more of which can be incorporated. An alternate anti-rotation design is shown in FIG. 5. FIG. 5 is a plan view of the cup in which the cross-section of the conical element is slightly oval to prevent rotation.

The cup can be made from any suitable material, for example, a synthetic plastics material such as ultra high molecular weight polyethylene or a metal and, as mentioned above, can be made in any convenient form, for example, with plastic bearing inserts or other features.

While several examples of the present invention have been described, it is obvious that many changes and modifications may be made thereunto, without departing from the spirit and scope of the invention.

We claim:

1. An acetabular prosthesis for cementation with bone cement to a prepared natural acetabulum, comprising:

a cup-shaped portion having a tapered outer surface and an inner surface for receiving the ball of a femoral component, said tapered outer surface forming an apex at a proximal end of said cup-shaped portion; and an enclosure element bonded to the bone cement and located on said apex at the proximal end of said cup-shaped portion, said enclosure element having an open distal end and a closed proximal end wherein said open end has a tapered collar portion generally matching said tapered outer surface of said cup-shaped portion, said open end of said enclosure element having a diameter sized to create a void within the cement between said closed proximal end of said enclosure element and said apex upon engagement of said open end of said enclosure element with said outer surface of said cup-shaped portion whereby said void allows said proximal end of said cup-shaped portion to move further into said void within said enclosure element after implantation.

2. The acetabular prosthesis as set forth in claim 1 wherein said enclosure element is made of polymethylmethacrylate.

3. The acetabular prosthesis as set forth in claim 1 wherein said enclosure element is made of an acrylic material and is cup-shaped with side walls extending to the distal end of said cup-shaped portion after insertion thereon.

4. The acetabular prosthesis of claim 1 wherein said cup-shaped portion includes a means for preventing rotation thereof in the prepared acetabulum.

5. The acetabulum prosthesis as set forth in claim 1 wherein said outer surface of said cup-shaped portion is conically shaped.

6. A prosthetic acetabular component comprising:

a cup for cementation with bone cement to the natural acetabulum having an outer surface extending outwardly from an apex at a proximal end thereof and an inner surface for receiving the ball of a femoral component; and an enclosure element bonded to said bone cement and having an open end for enclosing at least the apex of said cup outer surface, said enclosure element having a closed proximal end and wherein said open end has a tapered collar portion for engaging the tapered portion of said cup outer surface, said tapered portion of said open end having an opening sized to create a space within the cement between said closed end of said enclosure element and said apex of said cup outer surface whereby said void allows said proximal end of said cup-shaped portion to move further into said void within said enclosure element after implantation.

7. The acetabular prosthesis as set forth in claim 6 wherein said enclosure element is made of polymethylmethacrylate.

8. The acetabular prosthesis as set forth in claim 6 wherein said enclosure element is made of an acrylic material and is cup-shaped with side walls extending to the distal end of said cup-shaped portion after insertion thereon.

9. The acetabular prosthesis of claim 6 wherein said cup-shaped portion includes a means for preventing rotation thereof in the prepared acetabulum.

10. The acetabular prosthesis as set forth in claim 1 wherein said outer surface of said cup-shaped portion is conically shaped.

* * * * *